(12) United States Patent
Cooper et al.

(10) Patent No.: US 9,861,526 B1
(45) Date of Patent: Jan. 9, 2018

(54) PROGRAMMABLE PATTERNING AND MASKING ARRAY FOR CORNEAL COLLAGEN CROSSLINKING

(71) Applicant: TECLens, LLC, St. James, NY (US)

(72) Inventors: Frank George Cooper, Dix Hills, NY (US); Patrick David Lopath, Stamford, CT (US)

(73) Assignee: TECLens, LLC, St. James, NY (US)

( * ) Notice: Subject to any disclaimer, the term of this patent is extended or adjusted under 35 U.S.C. 154(b) by 41 days.

(21) Appl. No.: 14/751,358

(22) Filed: Jun. 26, 2015

Related U.S. Application Data

(60) Provisional application No. 62/018,943, filed on Jun. 30, 2014.

(51) Int. Cl.
*A61F 9/01* (2006.01)
*A61F 9/008* (2006.01)

(52) U.S. Cl.
CPC ........ *A61F 9/00827* (2013.01); *A61F 9/0084* (2013.01); *A61F 2009/00842* (2013.01); *A61F 2009/00872* (2013.01); *A61F 2009/00893* (2013.01)

(58) Field of Classification Search
CPC .............................. A61F 9/008–9/0084; A61F 2009/00842–2009/00897
See application file for complete search history.

(56) References Cited

U.S. PATENT DOCUMENTS

| | | | |
|---|---|---|---|
| 6,436,093 B1* | 8/2002 | Ruiz | A61F 9/00808 606/4 |
| 2008/0015660 A1* | 1/2008 | Herekar | A61N 5/062 607/88 |
| 2013/0211389 A1 | 8/2013 | Chuck et al. | |
| 2014/0379054 A1 | 12/2014 | Cooper et al. | |
| 2015/0313756 A1* | 11/2015 | Skerl | A61F 9/008 606/3 |
| 2015/0374540 A1 | 12/2015 | Lopath et al. | |

* cited by examiner

*Primary Examiner* — Michael Kahelin
(74) *Attorney, Agent, or Firm* — Lerner, David, Littenberg, Krumholz & Mentlik, LLP

(57) ABSTRACT

The present application relates generally to a method for vision correction using corneal collagen crosslinking ("CCXL"), in which the physician is able to precisely control the pattern of ultraviolet ("UV") energy delivered to the cornea, by means of a programmable masking array placed between the UV source and the cornea. A CCXL LCD masked is used to create various patterns of "on" and "off" pixels. The physician is able to control the degree of polarization of the LCD pixels, thereby allowing the physician to create various patterns of UV irradiation and thus, varying levels of CCXL.

4 Claims, 5 Drawing Sheets

PROGRAMMABLE PATTERNING AND MASKING ARRAY FOR CORNEAL COLLAGEN CROSSLINKING

CROSS-REFERENCE TO RELATED APPLICATIONS

The present application claims the benefit of the filing date of U.S. Provisional Patent Application No. 62/018,943, filed Jun. 30, 2014, the disclosure of which is hereby incorporated herein by reference.

BACKGROUND OF THE INVENTION

Corneal collagen crosslinking (CCXL) has been used since the late 1990s to treat keratoconus. Recently it has been applied to healthy eyes to affect refractive changes in the shape of the cornea, and to eyes with certain antibiotic resistive infections.

The standards of corneal collagen crosslinking for treatment of keratoconus set the dose at an energy per area of 3 mW/cm2, delivered uniformly over the center 8 mm of the cornea for 30 minutes. This sums to about 5.4 J/cm2 of energy, or a total of about 2.7 J. However, the goals of CCXL for refractive correction (and anti-infective use) are different than that of keratoconus treatment, and thus the dosimetry, typically differ from this standard protocol.

CCXL for vision correction achieves refractive shape change of the cornea by creating chemical bonds between the protein layers in the corneal stroma. These bonds (cross-links) increase the stiffness of the cornea in the region crosslinked. This increased stiffness changes the balance between the cornea tension and the intraocular pressure. Through mechanisms not completely understand in the industry, within a few days of CCXL therapy, physiologic processes reshape the cornea. The amount of reshaping, and thus the degree of curvature correction, is determined by a number of treatment parameters, including the amount and rate of energy delivery, the treatment time, and the shape and size of the treated area on the cornea. For myopia (near-sightedness), the center of the cornea is stiffened; for hyperopia (farsightedness), an annulus around the periphery of the cornea is stiffened. For more complicated corrections such as astigmatism, custom patterns are used.

Currently, there exists a fixed optical mask that is placed on the cornea in the form of an etched contact lens patterned to spatially modulate the UV dose delivered across the cornea. However, by this method, a custom-etched contact lens would have to be provided for each individualized patient prescription.

DETAILED DESCRIPTION

Figure 1:
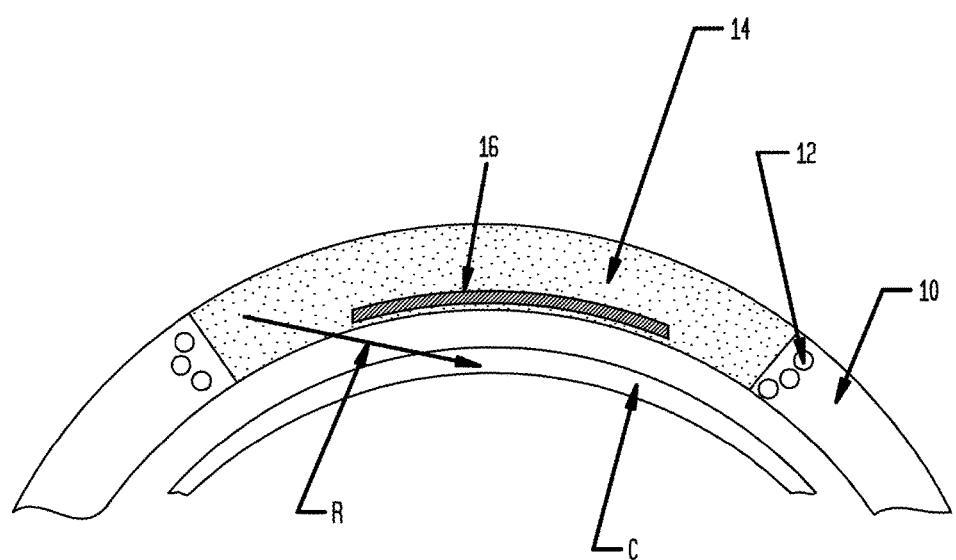
FIG. 1 is a diagrammatic sectional view of a device according to one embodiment of the invention.

One aspect of the invention described herein provides a method to precisely control the pattern of UV energy delivered to the cornea during the crosslinking procedure by means of a programmable masking array placed between the UV source and the cornea. Preferred methods and apparatus according to this aspect of the present invention accomplishes the masking in a controllable manner, creating programmable patterns on the contact lens using technologies typically employed in image displays. The mask patterns can be customized in real time, and can even be varied throughout the CCXL treatment if necessary as regions reach the desired amount of crosslinking. This customized or 'live' mask can provide real time 3 dimensional control of administered dose (X, Y, and time) across the corneal surface. The customization optionally can be coupled with a point by point feedback system (i.e., acoustic or optical spectral reflected spectral analysis) that is capable of monitoring the degree of cross-linking achieved at multiple points in the cornea during the CCXL treatment. One form of feedback system capable of providing such monitoring is disclosed in the commonly assigned U.S. Provisional Patent Application entitled "Real Time Acoustic Dosimetry For Corneal Collagen Crosslinking," filed on Jun. 27, 2014, which is incorporated in this application in its entirety.

Apparatus according to one aspect of the invention utilizes a thin array of liquid crystal display (LCD) "pixels." The array consists of a layer of liquid crystals that are able to change the polarization of light passing through them, sandwiched between two orthogonal polarizers and a patterned electrode array to control the degree of polarization of the liquid crystals. Unlike most modern image displays, the CCXL mask presented here does not employ an array of colored sub pixels; it is monochromatic, effectively transparent, or black. In one embodiment, twisted nematic liquid crystals are used to rotate the polarization of the light passing through; however, other types of liquid crystals, with different mechanisms of interaction with the polarization of the incident light can also be employed as UV masks. As some liquid crystals are damaged by UV exposure, and others are non-transparent to UV even in the "on" state, care must be taken to select materials that will function appropriately. There are factors working in favor of a reasonably broad field of liquid crystal material selection for those skilled in the art such as the facts that the CCXL procedure is neither very long (typically under 30 min), nor very high intensity UV (typically 3 mW/cm2 to 30 mW/cm2). Additionally, the wavelength used is long or UV, around 360 nm to 380 nm, thus comparatively low energy.

In its simplest embodiment, the LCD mask presented herein is used in conjunction with a standoff UV source. In this approach, UV light is generated a few centimeters away from the target eye with the LCD masking contact lens in place. Light generated at a distance from the eye provides roughly collimated rays impinging on the eye, so the planned crosslinking treatment pattern can be mimicked in the programmable mask pattern. The pixels of the masking array can be controlled over a given dynamic range of light transmission by manipulating the degree of polarization of the liquid crystals, going from full dark to fully transparent, enabling a customized CCXL pattern to be created on the eye from essentially a uniformly flooding UV source.

One of the challenges of a stand-off UV source for CCXL is patient motion. By using this on cornea mask with a standoff light source, it is possible to use some or all of the LCD pixel pattern as fiducial marks for a UV light alignment system. If, for example, the LCD were patterned onto a scleral type contact lens a lens design that moves very minimally with respect to the corneal surface CCXL UV delivery system employing a stand off UV source that was able to move in X and Y (with the optical axis of the eye as Z) could be coupled with an imaging and analysis approach to move the UV source in response to gross patient movements during the procedure. The area flooded with UV would track the LCD pattern, limiting UV exposure to areas other than the target region on the cornea.

Another significant drawback of stand-off UV sources is the need for the patient to have the eyelid of the target eye retracted with a speculum. Along the same lines as fiducial markers to track motion, specifically designed LCD pixel patterns outside the area of UV irradiation can be used as a blink detectors for non-speculum CCXL procedures with a stand off light. Once the mask lens is in place on the eye, pixels outside treatment region that are very near the eyelids (particular to that patient, as everyone's eyelids are different) could be darkened. If the image capture system fails to "see" one of these marks during the procedure, the eyelid must be closing, and the UV can be shut off.

The more preferred embodiment of the LCD mask is to be built into an on-eye CCXL UV delivery device. Such devices are taught in Chuck et al., U.S. Patent Application Publication No. 2013/0211389 A1 ("Chuck"); in Cooper et al., U.S. Provisional Patent Application No. 61/839,016, filed Jun. 25, 2013 ("Cooper '016"); and in Cooper et al., U.S. patent application Ser. No. 14/314,518, filed Jun. 25, 2014 ("Cooper '518"), the disclosures of which are incorporated herein. Certain devices according to Cooper '016 and '518 and Chuck have form and size similar to that of a conventional contact lens.

In certain embodiments disclosed in Cooper '016 and '518, a uniform UV back light is created by directing light into a dispersive element such as a plastic or silicone material bulk loaded with very small UV scattering particles. The dispersive element may be in the form of a layer or shell with an inner surface facing toward the eye and an outer surface facing away from the eye, and with edge surfaces extending between the inner and outer surfaces. Light may be supplied to the dispersive element by emitters such as LEDs mounted to the structure itself or by a transmission fiber extending to the structure from a light source remote from the eye. No additional light diffusers are necessary with this backlight method. In other embodiments, the dispersive element may include a total internal reflector formed from a transparent material with numerous reflecting points such as features in one or more surfaces of the element as, for example, in the outer surface of the element facing away from the eye. A dispersive element of this type may be similar to the elements used in backlighting in modern video monitors. Typically, a further light diffuser is used in conjunction with a dispersive element of this type.

One challenge of effectively masking "on-lens" generated UV light created with an edge light system (with either reflective diffusers or with the bulk scatter approach) is the fact that light rays created are not collimated, and thus on a curved lens, a mask may not be exceedingly effective at preventing UV exposure to areas of the cornea directly below the mask. This is the parallax problem displayed in FIG. 1.

There are a number of ways to address the parallax issue. Easiest is an embodiment where the internal reflecting light guide that carries the light from the edge source is extremely thin. In Cooper '016 and '518, this means no thicker than the diameter of a single fiber optic fiber. With an LED perimeter array, the die size and orientation of the LEDs will dictate the minimum thickness. It is easy to see from FIG. 1 that the thinner the scatterer, the less parallax comes into play.

A second parallax defeating measure, preferably used in conjunction with a thin internal reflective light guide, is a collimator. These devices are typically used as "privacy filters" on laptop displays. They prevent a viewer from looking at information displayed on the screen form the side. Most common is the "microlouver" technology from 3M. There are two approaches to using this privacy technology as a collimator to eliminate the parallax challenge to UV masking for CCXL. In one embodiment, the microlouver device would essentially be mounted "inside out," above (on the outer or eyelid side) of the LCD mask, between the LCD mask and the scattering internal reflector. Mounting the privacy louver "inside out" means that the face of the louver that would typically face out toward the eye of the viewer (of the display screen for which they were originally designed) is turned to face toward the light guide (away from the eye of the patient). In this manner, only light that scatters perpendicular to the plane of the LCD (or normal to the spherical surface if the LCD is curved) is allowed to pass through the collimator to in turn either hit the cornea or be blocked by the mask. This eliminates light rays from the side that could get around the mask and will provide very precise boundaries between "on" pixels and "off" pixels. Effectively, this is a high-pass spatial filter.

The potential problem with this inside-out approach is attenuation of the UV light. Depending on the desired UV intensity in the non-masked areas, an ordered optical stack of "light guide to collimator to mask" may reduce the therapeutic UV intensity out of the desired range. The polarizing filters on the LCD itself can further attenuate the scattered light energy coming out of the light guide. Modern LCDs deal with this attenuation by using a reflective polarizer between the light guide and the liquid crystals. With a reflective polarizer, the light that is "off-polarization" from the filter is reflected back into the light guide to be rescattered and given a second chance (and third, fourth, etc.) at arriving at the polarizer with the correct polarization.

An alternative approach to help mitigate this attenuation is to use the privacy filter as designed, layering it on the front or inner a side of the LCD mask, i.e., the side of the LCD mask facing toward the cornea. In this embodiment, correctly polarized light from scatterers that are not directly above the LCD pixel can enter the LCD mask, increasing the brightness coming out of the "on" pixels. The trade-off is that the spatial bandpass frequency has been lowered to some degree with "off-axis" rays able to enter the LCD. These rays will blur the line between "on" and "off" pixels, effectively reducing the contrast. The closer the LCD mask is to the corneal surface, the less this blurring will be. Given that the CCXL procedure is based on the creation of reactive free radical species in the cornea, and that the diffusion distances of these species during the treatment time is currently unknown in the field (but likely not to be extremely short), some blurring of the crosslinking effect at the pixel boundaries is likely anyway due to the fundamental physiology of the procedure. As understanding of this phenomenon improves, it may become more critical to tightly control the spatial frequency capabilities of the mask/filter arrangement. Alternatively, it may become apparent that some blurring of the lines do to off-axis rays is totally acceptable.

Brightness enhancer films can be employed to direct the scattered light forward. This approach can exceed collimators in terms of the amount of light it lets through. Enhancer films use tiny prisms to redirect (refract) the light rays from the backlight, emitting them directionally toward the observer. While not true collimation, these enhancers reduce the parallax problem significantly without losing brightness. For operation in UV, these enhancers can be made very thin. One type of enhancer film incorporates an array of prisms extending parallel to one another. These prisms are arranged to narrow the spreading angle of light in one plane. In one embodiment, two such enhancers are arranged so that their narrowing planes are orthogonal to one another. The two orthogonal enhancers are placed between the dispersive element and the reflective polarizer of the LCD. This optical stack should exhibit a slightly lower frequency cut-off for spatial resolution (meaning some additional blurring of "on" and "off") than either of the microlouver collimator embodiments, but will provide much more light to the cornea.

The LCD mask can be used to create various patterns of "on" and "off" pixels. These pixels are programmable in that they can be turned "on" (transparent) or "off" (black) at any point before or during the procedure. The pixels can also be controlled to be partially "on" or "off" by modulating the control voltage levels in either active mode (with thin film transistors, as used in most modern mobile technology screens) or passive mode (a simple conductor grid used on most older LCD video display screen). Passive LCD displays have fallen out of favor due to slow refresh rates and poor viewing angles, neither of which are concerns for a CCXL LCD mask.

Figure 2:
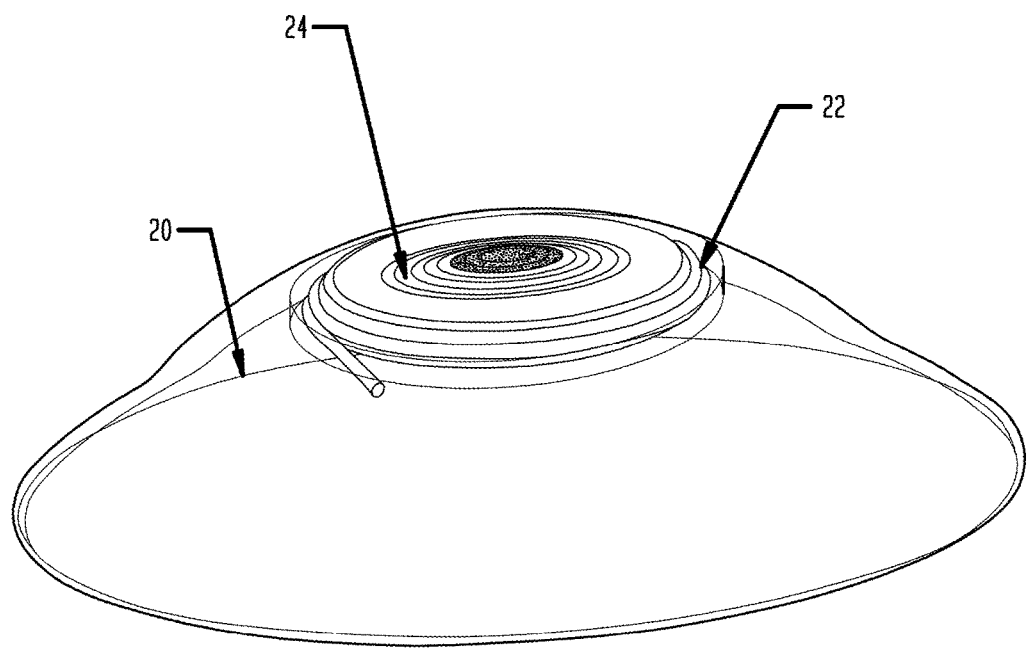
FIG. 2 is a diagrammatic perspective view of a device according to a further embodiment of the invention.

These aspects of spatial and intensity control allow the physician to create various patterns of UV irradiation (and thus varying levels of corneal collagen crosslinking) on the cornea to affect the desired therapeutic outcome, be that corneal stability, corneal shape change, anti-infection care, or treatment of other corneal maladies. In one embodiment for the treatment of myopia and hyperopia, the pixels are arranged in an annular pattern, with a center circle, and surrounding annular rings. For one particular case, the center pixel is set to approximately 1 mm in diameter, with 7 surrounding ½ mm wide annular rings, for a total of 8 pixel elements. For treatment of myopia, the center pixel or pixels (depending on the physician defined prescription) would be "on," allowing UV to pass through, and the peripheral rings would be "off," limiting the size of the CCXL spot in the center of the corneal. (FIG. 2.)

Figure 3:
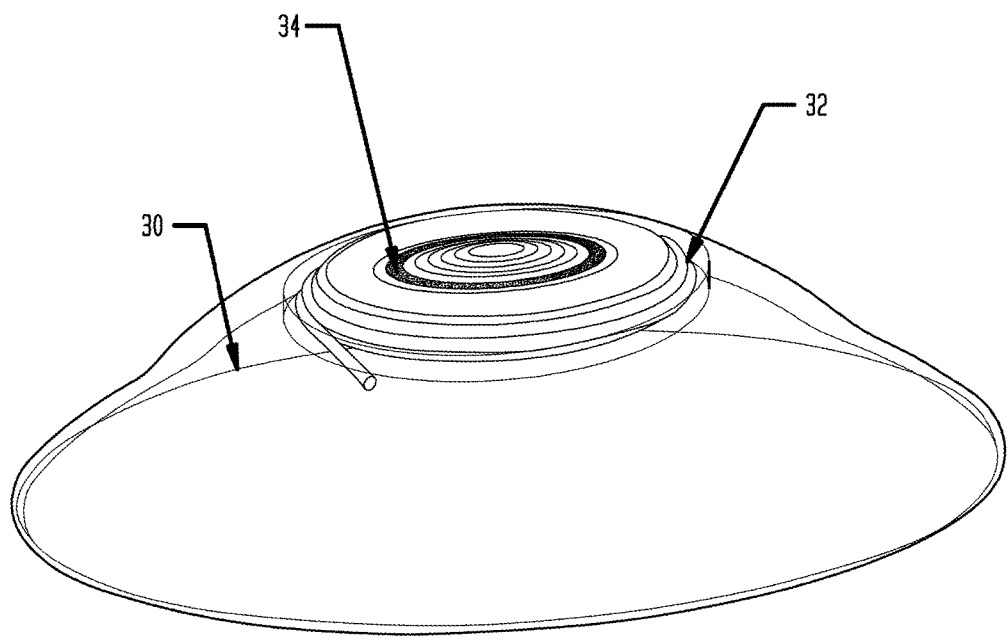
FIG. 3 is a diagrammatic perspective view of a device according to a further embodiment of the invention.

Various methods can be used to determine the size of the CCXL spot, some of these based on modifications of the Munnerlyn formula used in laser ablative corneal correction. For treatment of hyperopia, the opposite pattern of "on" and "off" pixels would be created, with the center pixels "off" (black) and the outer rings "on" to create a crosslinked annulus around the periphery of the cornea. (FIG. 3.)

Figure 4:
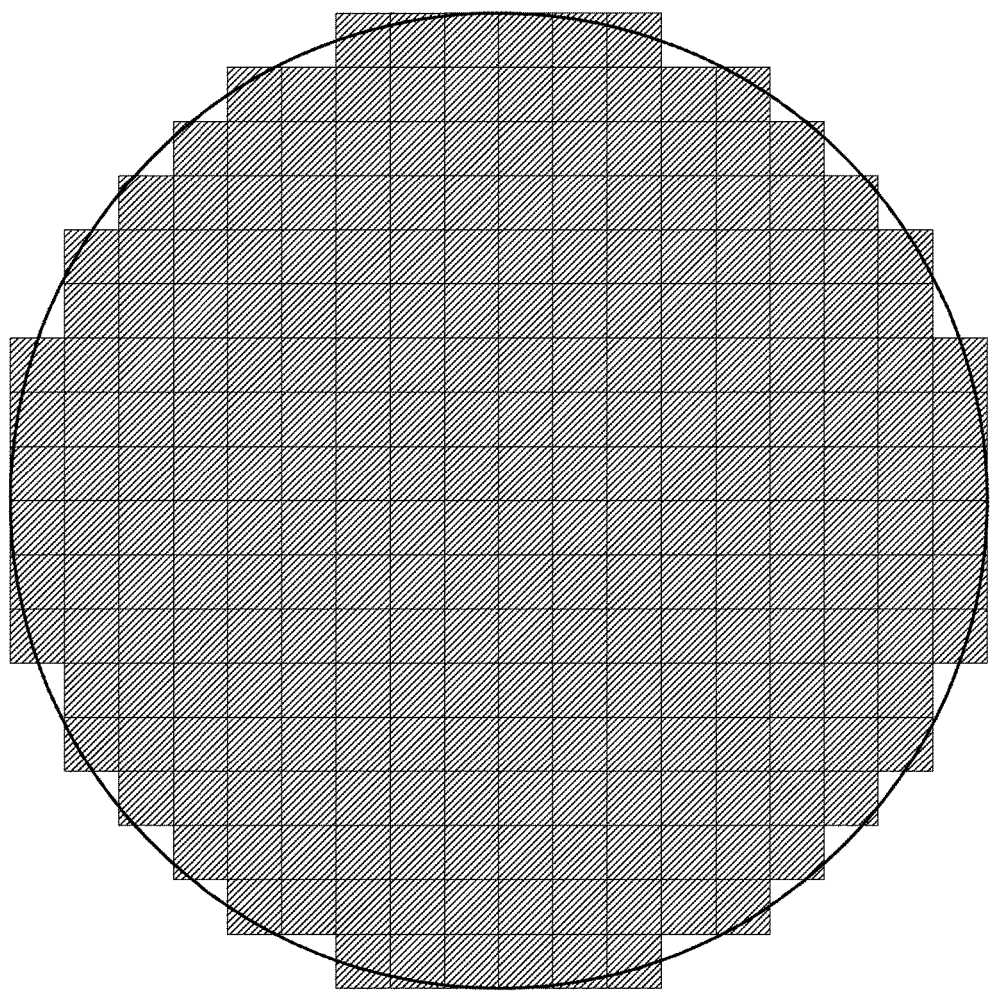
FIG. 4 is a diagrammatic plan view depicting an element used in certain embodiments of the invention.
Figure 5:
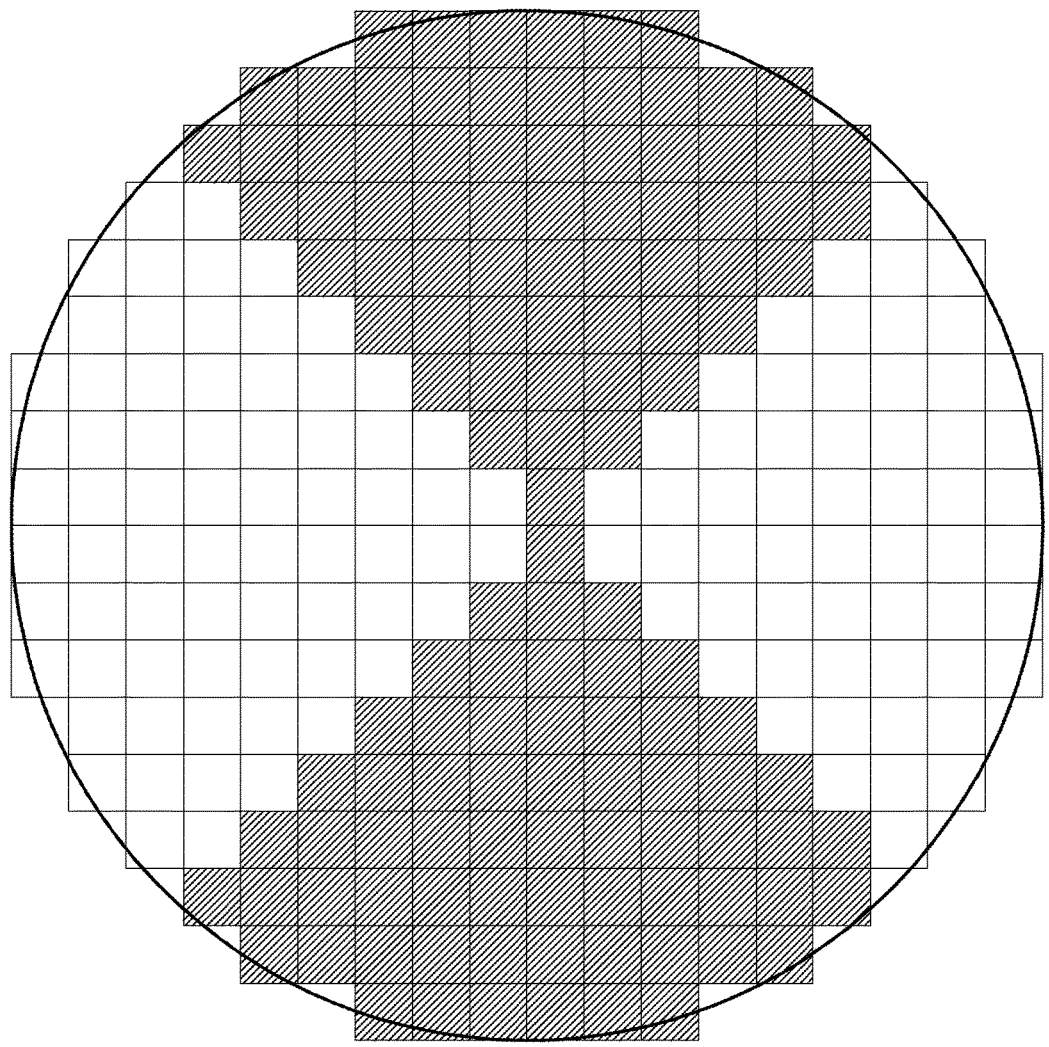
FIG. 5 is a diagrammatic plan view depicting an element used in other embodiments of the invention.

For the treatment of more complex corneal shape irregularities such as astigmatism, a rectangular grid pattern of LCD pixels is defined to enable the physician to define the UV irradiate zone. In one embodiment, 256 rectangular pixels are defined to cover the central 8 mm of the cornea. (FIG. 4.) For astigmatism, typically some type of "butterfly" pattern of UV exposure is used to compensate for the uneven curvature of the astigmatic cornea. (FIG. 5.)

Control of the LCD pixels can be achieved in a number of different ways. In most embodiments, an on-lens application specific integrated circuit (ASIC) is used to receive, decode and distribute the addressing and intensity information. Specifically, the ASIC modules include a universal asynchronous receiver transmitter (UART), a voltage regulator and charge pump for LCD "on"/"off" control, serial data to pixel address and intensity information converter, memory, and a self-test system. In one embodiment consistent with Cooper '016 and '518's approach of delivering the UV edge light to the lens with an optical fiber, the pixel data is delivered serially over the same fiber by modulating the UV light or by supplying modulated light at a wavelength different from the UV light. A PIN photodiode receiver on an ASIC converts the modulated light to an electrical signal which is passed to the UART. For single frequency operation, the addressing and intensity information is modulated onto the UV light prior to initiation of the corneal treatment, with updates to the pixel pattern delivered during any dark periods of treatment duty cycling. For dual frequency operation, the data is send to the LCD controller on a second optical wavelength simultaneously carried on the fiber and filtered from the therapeutic energy prior to the PIN diode receiver.

In another embodiment, communication of the pixel information is accomplished directly using electrical leads. Given the extremely low power requirements of LCD pixels, one version of the electrical communication approach is paired with a Cooper-type fiber optic lens with 3 very fine wires loosely spiraled around the fiber carrying the UV. These leads carry: (1) the communication signal, (2) the "high" voltage, V+, and the signal and power ground or "common" voltage. In some embodiments, the communications lead is bi-directional to enable parity checking.

The low power requirements of LCD pixels enables other embodiments for either (or both) power or (and) information delivery via wireless communications. One embodiment uses near field communications and power transfer. In some embodiments, a loop antenna is used in the manner of U.S. Patent Application Publication No. 2010/0103368 A1, filed Apr. 29, 2010, entitled "Active Contact Lens." In other embodiments, a fine wire antenna is brought up off the lens along the fiber optic connection; spiraled where necessary to add length to help match energy field frequencies.

Although the embodiments discussed above use UV light to promote cross-linking, other embodiments of the present invention can use light at other wavelengths effective to activate a cross-linking agent. For example, where riboflavin is applied to the eye as a cross-linking agent, visible light in the blue wavelength band can be employed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

FIG. 1 depicts the parallax problem: UV ray scattered from a more peripheral area of the CCXL lens can pass under the LCD mask because of the thickness of the scattering material and the curvature of the lens. Reference numeral 16 represents the LCD mask. Reference numeral 14 represents silicone with UV scatterers in the bulk. Reference numeral 12 represents edge light fiber optic loops, seen in cross-section. Reference numeral 10 represents the lens-based CCXL system after chuck. Reference character R represents UV ray scattered under the mask. Reference character C represents the cornea.

FIG. 2 depicts a myopia treatment configuration of annular LCD pixels. Reference numeral 24 represents an annular array of LCD "pixels" with central elements transparent to UV for myopia therapy. Reference numeral 22 represents fiber optic IV edge light after Cooper[3].

FIG. 3 depicts a hyperopia treatment configuration of annular LCD pixels. Reference numeral 34 represents an annular array of LCD "pixels" with peripheral elements transparent to UV for hyperopia therapy. Reference numeral 32 represents fiber optic UV edge light after Cooper[3]. Reference numeral 30 represents crosslinking CCXL contact lens after Chuck[2].

FIG. 4 depicts a 0.44 mm pitch array of 256 rectangular LCD pixels to cover the central 8 mm of the cornea.

FIG. 5 depicts an example of using a grid of LCD pixels to mask out the top and bottom of the cornea to create a "butterfly" pattern of UV irradiation to treat astigmatism.

The invention claimed is:

1. A method of vision correction comprising:
    positioning a structure incorporating an LCD mask and an optically scattering element on an anterior surface of an eye so that the LCD mask is disposed near the cornea of the eye and disposed between the scattering element and the cornea;
    applying light energy to the cornea by directing light into the scattering element so that light scattered in the scattering element passes through the LCD mask to stimulate corneal crosslinking;
    controlling transmission of the light energy through individual pixel elements of the LCD mask to control the pattern of light energy delivered to the cornea during the crosslinking procedure.

2. The method of claim 1, wherein the step of controlling the transmission of light energy includes controlling some of the pixel elements to transmit the light energy and controlling others of the pixel elements to block the light energy.

3. The method of claim 1, wherein the step of controlling the transmission of light energy includes varying the transmission of the light energy through at least some of the pixel elements during the step of applying light energy.

4. The method of claim 1, further comprising the step of monitoring the degree of crosslinking achieved at multiple points during the step of applying light energy.

* * * * *